United States Patent [19]
Watrous

[11] Patent Number: 5,947,909
[45] Date of Patent: Sep. 7, 1999

[54] NEURAL NETWORK POLYMORPHIC QRS DETECTOR

[75] Inventor: Raymond L. Watrous, Kingston, N.J.

[73] Assignee: Siemens Corporate Research, Inc., Princeton, N.J.

[21] Appl. No.: 08/994,179

[22] Filed: Dec. 19, 1997

[51] Int. Cl.⁶ .................................................. A61B 5/0456

[52] U.S. Cl. ............................................................ 600/521

[58] Field of Search ..................................... 600/521, 508, 600/509

[56] References Cited

U.S. PATENT DOCUMENTS

| 5,524,631 | 6/1996 | Zahorian et al. | 128/698 |
| 5,598,508 | 1/1997 | Goldman | 395/22 |
| 5,630,019 | 5/1997 | Kochi | 395/22 |

*Primary Examiner*—Scott M. Getzow
*Attorney, Agent, or Firm*—Lawrence C. Edelman

[57] ABSTRACT

A large universe of signals can be rapidly examined for a specific phenomenon by searching for a morphology representative of a subgroup of the universe. A detector for each such representative morphology is arranged in parallel to examine a signal input and provide an indication of positive identification a specific morphology.

8 Claims, 2 Drawing Sheets

NEURAL NETWORK POLYMORPHIC QRS DETECTOR

Physical phenomena, such as heartbeats, can vary from one person to the next, and perhaps from one event to the next within the same individual. Consequently, devices that sense these phenomena, such as electrocardiogram sensors, may display different morphologies and timings for different events. Similarly, multiple sensors observing a single phenomenon may vary due to positional differences. Thus, a single mechanism that can detect specific events in such signals in a large population would need to handle a wide variety of inputs.

Typically, event detectors have operated on the assumption that there is a single, unique characteristic present in all possible morphologies. By searching for this characteristic, detection can be accomplished. However, identifying such a characteristic may not be possible and devices attempting to operate in this fashion may not provide the desired level of accuracy.

If one assumes that the population can be subdivided into clusters of similar or characteristic morphologies, the entire population can then be represented by a set of the representative morphologies. Once the representative morphologies are identified, detectors can be obtained to detect each of the morphologies. The detectors can be connected in a parallel bank and each simultaneously receive input from the phenomenon under observation, a person in the case of an electrocardiogram. Whenever a valid morphology from the population is presented, a positive indication will appear at the output of the detector bank.

DESCRIPTION OF THE INVENTION

Figure 1:
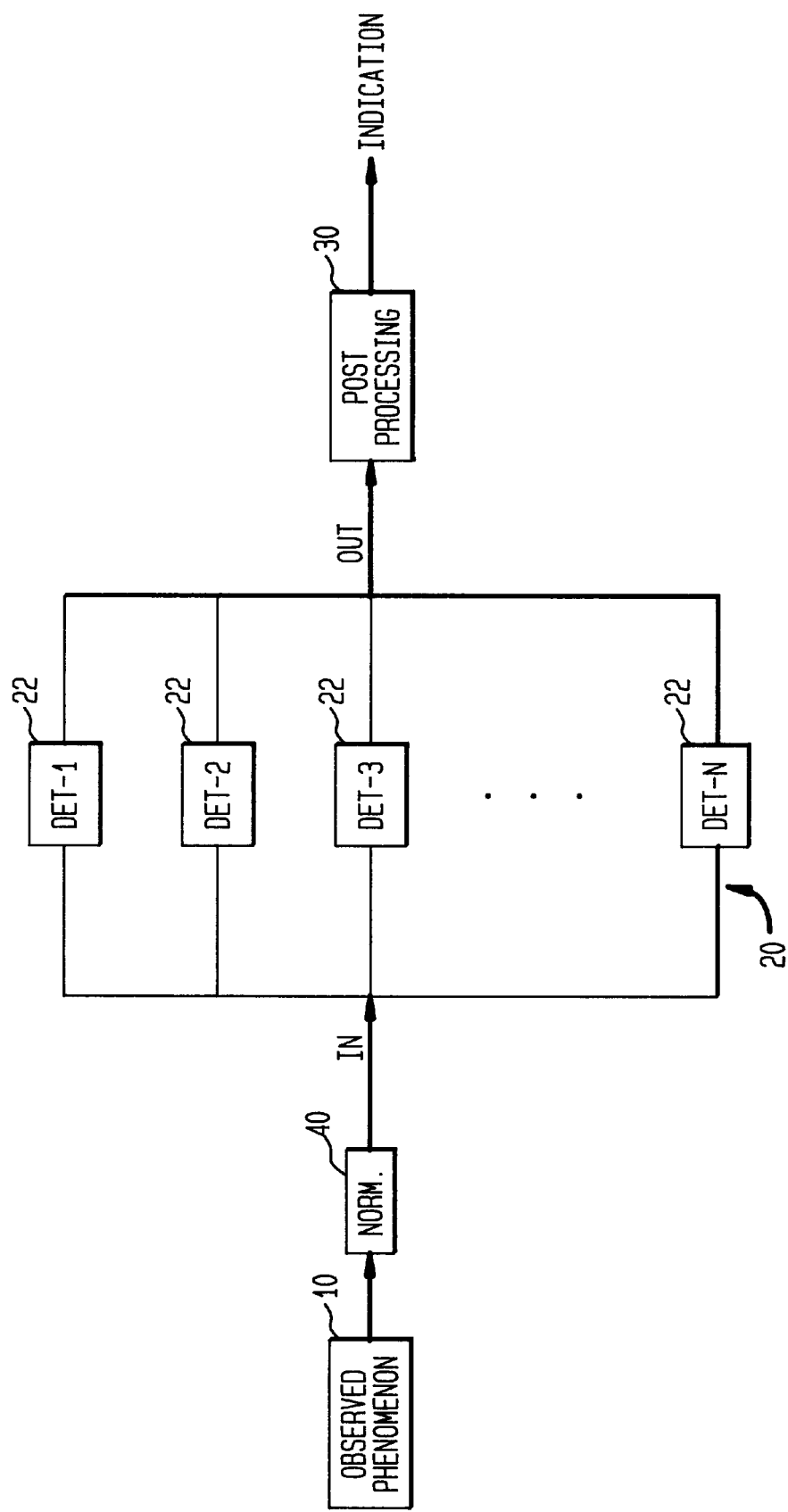
FIG. 1 is a block diagram of an apparatus for detecting events within waveforms.

An apparatus for detecting events within a waveform is shown in FIG. 1. An observed phenomenon 10 provides a continuous time-varying signal believed to contain certain repeating phenomena within a particular waveform. The signal is provided simultaneously to a bank 20 of detectors 22, arbitrarily designated "DET-1, DET-2, . . . DET-N," connected in parallel. The detectors 22 can be any device that will detect a waveform or morphology. Suitable devices are artificial neural networks, matched filters, adaptive filters, fuzzy networks, rule-based expert systems, syntactic or probabalistic pattern matchers, and similar devices. The outputs of the individual detectors 22 are ORed together. To insure that a single morphology will not give rise to multiple detections, a post-processing module 30 with hysteresis can follow the detector bank 20.

Figure 2:
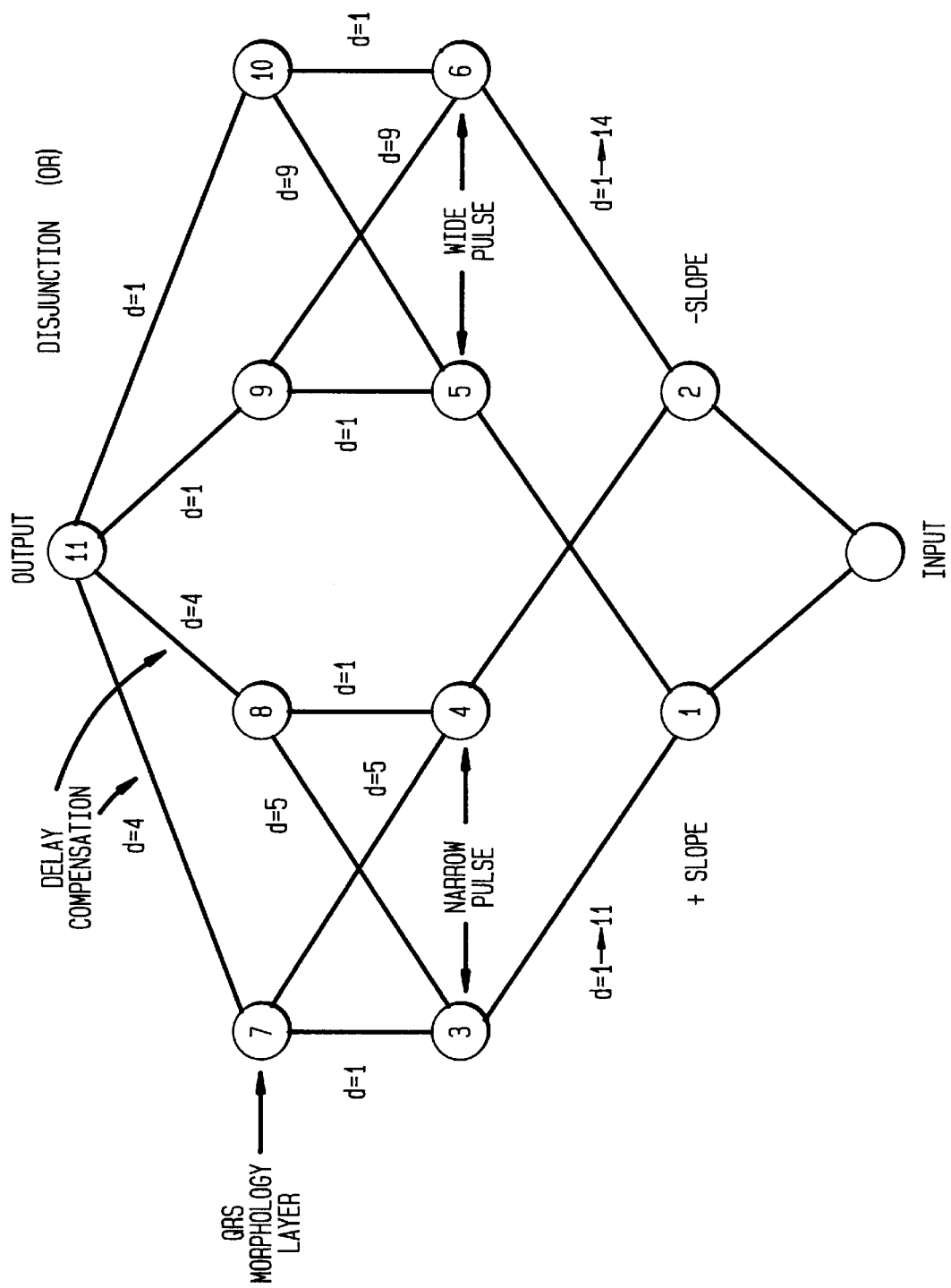
FIG. 2 is a diagram of an artificial neural network that may be employed for the detectors in the apparatus of FIG. 1.

As noted, an artificial neural network can be employed as a detector. These networks can be trained, or constructed by hand and then perhaps trained, as those skilled in the art understand. Clustering algorithms can also be used to obtain representative morphologies and similarly determine the number of such representative morphologies that would be required to model the entire population. A hand-constructed network that will detect QRS events in an electrocardiogram is shown in FIG. 2. This particular network has input and output layers and three hidden layers connected with delays as indicated. The first hidden layer (units 1 and 2) detects the slope of the input signal. The second hidden layer (units 3–6) detects the duration of the slopes of the input signal (narrow and wide pulses). Finally, the third hidden layer (units 7–10) are conjunctively responsive to certain combinations of units in the second hidden layer and detect particular morphologies. The output layer (unit 11) is disjunctively responsive to the units of the third hidden layer.

The actual delays employed and the weights assigned will depend on the particular morphology under study. However, in the example of FIG. 2, the weights assigned to the first layer sum to zero to achieve level independence.

Instead of hand constructing the network, the weights could be randomly assigned and then adjusted by training. Artificial neural networks can be trained using methods discussed in Watrous, Raymond L., "Learning Algorithms for Connectionist Networks: Applied Gradient Methods for Nonlinear Optimization," *First International Conference on Neural Networks,* San Diego, Calif., June 1987, vol. II, pp. 619–27; and Wasserman, Philip D., *Advance Methods in Neural Computing,* New York: Van Nostrand Rheinhold, 1993, incorporated herein by reference.

In some populations, amplitude may vary from one morphology to the next. A gain normalizer 40 may be inserted ahead of the detector bank 20 to account for this variation.

What is claimed is:

1. An apparatus, comprising:
   a signal input for accepting a continuous time-varying signal;
   a plurality of detectors, each detector having an input and an output, where the inputs of the detectors are continuously responsive to the signal input; and
   a detection output, where the detection output is responsive to the outputs of the detectors.

2. An apparatus as set forth in claim 1, where the detectors are responsive to morphologies of the input signal, and each detector is responsive to a unique morphology.

3. An apparatus as set forth in claim 1, where the detectors comprise one or more from the group of artificial neural networks, matched filters, adaptive filters, fuzzy networks, rule-based expert systems, and syntactic and probabalistic pattern matchers.

4. An apparatus as set forth in claim 1, where the detectors comprise artificial neural networks, each network comprising a plurality of layers responsive to the slope of the input signal and/or the duration of the slopes of the input signal.

5. An apparatus as set forth in claim 1, further including means for normalizing the gain of the input signal.

6. An apparatus as set forth in claim 1, further including means for introducing hysteresis to the output signal.

7. A QRS detector, comprising:
   a electrocardiogram signal input;
   a plurality of QRS detectors responsive to morphologies of the electrocardiogram signal, each detector being responsive to a unique morphology, and the detectors comprise means for providing an output indicative of a positive detection of a unique morphology; and
   a detection output, where the detection output is responsive to the detectors.

8. A method of detecting QRS signals, comprising the steps of:
   obtaining an electrocardiogram signal;
   providing the electrocardiogram signal to a plurality of QRS detectors, where the detectors are responsive to the electrocardiogram signal and each detector is responsive to a unique morphology; and
   scanning the detectors for an indication of detection.

* * * * *